US00PP09460P

United States Patent [19]

Hvid

[11] Patent Number: Plant 9,460

[45] Date of Patent: Feb. 27, 1996

[54] BEGONIA PLANT NAMED 'EDINBURGH'

[75] Inventor: Soren Hvid, Aarup, Denmark

[73] Assignee: L. Daehnfeldt A/S, Odense, Denmark

[21] Appl. No.: 385,183

[22] Filed: Feb. 7, 1995

[51] Int. Cl.[6] ..... A01H 5/00

[52] U.S. Cl. ..... Plt./87.18

[58] Field of Search ..... Plt./87.17, 87.18

*Primary Examiner*—James R. Feyrer

*Attorney, Agent, or Firm*—Foley & Lardner

[57] ABSTRACT

A new cultivar of Begonia named 'Edinburgh' characterized by a tall and reasonably branching growth habit; simple, alternate, medium green, double-serrated foliage that is generally orbicular and purple-red flowers on a sturdy peduncle with 12 or more tepals.

1 Drawing Sheet

The present invention relates to a new and distinct cultivar of begonia plant, botanically known as *Begonia hiemalis* (Fotsch), and known by the cultivar name 'Edinburgh.'

The new cultivar 'Edinburgh' is the product of a planned breeding program. The female or seed parent was a proprietary tuberous Begonia selection designated Code No. 1004890-1 and the male or pollen parent was a proprietary selection of *B. socotrana* designated Code No. 109. 'Edinburgh' was asexually propagated for the first time in May 1990 in Marslev, Denmark. Continuous asexual propagation by tip cuttings has demonstrated that the combination of characteristics as herein disclosed for the new cultivar 'Edinburgh' are firmly fixed and are retained through successive generations of asexual reproduction.

The following characteristics distinguish the new begonia from both its parent and other begonias commercially known and used in the floriculture industry:

1. 'Edinburgh' has purple-red flowers unlike any other known hiemalis begonia. It is more purple than 'Cheers' (U.S. Plant Pat. No. 6,013) or 'Lancelot' (U.S. Plant Pat. No. 6,928).

2. 'Edinburgh' is vigorous and tall like 'Schwabenland Red' (U.S. Plant Pat. No. 3,320) and 'Lancelot' but unlike the more compact variety 'Cheers.'

3. 'Edinburgh' has double flowers in contrast to the single flowers of 'Schwabenland Red.'

4. Foliage of "Edinburgh' is not as deeply lobed as those of 'Lancelot.'

5. The flowers of 'Edinburgh' are not ruffled like those of 'Cheers.'

'Edinburgh' has not been tested under all available environmental conditions and the phenotype may vary with variations in environmental conditions such as temperature, light intensity, daylength and humidity without a change in the genotype of the plant variety.

The accompanying color photograph taken August 1993 illustrates the overall appearance of this cultivar taken as an oblique view of the plant grown in 12 cm plastic pot and showing the colors as true as it is reasonably possible to obtain in a colored reproduction of this type.

The following is a detailed description of the new begonia cultivar based on plants produced under commercial practices in Hannover, Germany and Ashtabula, Ohio. Color references are made to The Royal Horticultural Society Colour Chart (R.H.S.) except where general terms of ordinary dictionary significance are use.

Parentage: *Begonia×tuberhybrida* designated Code No. 1004890-1 as seed parent and *Begonia socotrana* designated Code No. 109 as the pollen parent.

Propagation:

*Type cutting.*—Tip cutting 3 to 4 cm.

*Time to root.*—For planting 28–35 days at 22°–24° C. summer; for planting 35–42 days at 20°–22° C. winter.

*Rooting habit.*—Abundant, fibrous.

Plant description:

*Form.*—Tall, self-supporting, herbaceous.

*Habit of growth.*—Tall with acceptable branching from a pinch but late to flower.

*Foliage.*—Simple, alternate, medium green, double-serrated but not deeply cut. Size: 5–7 cm wide, 6–9 cm long. Shape: Generally ovate to orbicular, apices nearly acute, base unequal cordate. Texture: Glabrous. Margin: Doubly serrated, but not cut deep. Color: The topside of the young foliage is 146C R.H.S. with a very slight red margin while the underside is 146D R.H.S. The topside of the mature foliage is 146A R.H.S. while the underside is 146C R.H.S. Veination: Palmate.

Flowering description:

*Flowering habits.*—Indeterminate, late to flower under both short and long days; flowers borne upright and not pendulous; flowers are fully double.

*Natural flowering season.*—Year around.

*Flowers borne.*—On a study peduncle.

*Tepals.*—Color: The topside in winter when opening of the outer tepals is 57C R.H.S. with a margin that is 57A R.H.S. while the topside of the inner tepals is 58B R.H.S. The underside in winter when opening of the outer tepals is 51B R.H.S. the underside of the inner tepals 57A. Number of petals: 12 or more. Size of flowers: 5–6 cm.

*Reproductive organs.*—Pistils: None. Stamen: None.

I claim:

1. A new and distinct cultivar of Begonia named 'Edinburgh' as illustrated and described.

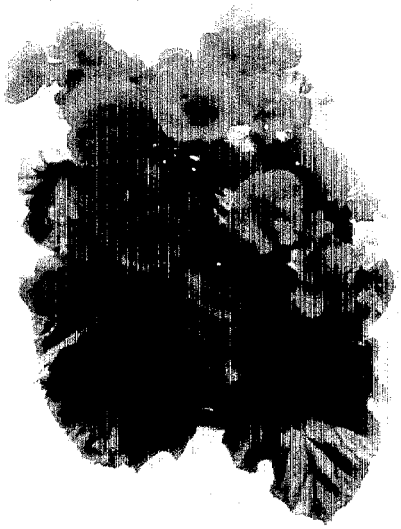

* * * * *